(12) United States Patent
Cavazza

(10) Patent No.: US 6,641,849 B1
(45) Date of Patent: Nov. 4, 2003

(54) **COMPOSITION FOR THE PREVENTION AND/OR TREATMENT OF CIRCULATORY DISORDERS, COMPRISING DERIVATIVES OF L-CARNITINE AND EXTRACTS OF *GINKGO BILOBA***

(75) Inventor: Claudio Cavazza, Rome (IT)

(73) Assignee: Sigma-Tau HealthScience S.p.A., Pomezia (IT)

( * ) Notice: Subject to any disclaimer, the term of this patent is extended or adjusted under 35 U.S.C. 154(b) by 0 days.

(21) Appl. No.: 10/110,018

(22) PCT Filed: Oct. 2, 2000

(86) PCT No.: PCT/IT00/00391

§ 371 (c)(1),
(2), (4) Date: May 7, 2002

(87) PCT Pub. No.: WO01/26666

PCT Pub. Date: Apr. 19, 2001

(30) Foreign Application Priority Data

Oct. 8, 1999 (IT) .......................................... RM99A0618

(51) Int. Cl.[7] .............................................. A61K 35/78
(52) U.S. Cl. ....................................... 424/757; 424/725
(58) Field of Search .................................. 424/725, 752

(56) References Cited

U.S. PATENT DOCUMENTS 5,861,434 A * 1/1999 Cavazza
6,221,356 B1 * 4/2001 Junsheng
6,306,392 B1 * 10/2001 Cavazza

FOREIGN PATENT DOCUMENTS

| EP | 0 733 020 A2 * | 5/1997 |
| WO | WO 98/33494 | 8/1998 |
| WO | WO 99/06039 | 2/1999 |

* cited by examiner

*Primary Examiner*—Leon B. Lankford, Jr.
*Assistant Examiner*—Ruth A. Davis
(74) *Attorney, Agent, or Firm*—Nixon & Vanderhye P.C.

(57) ABSTRACT

A composition is disclosed suitable for the prevention and/or treatment of circulatory disorders at both peripheral and cerebral level, and which can therefore take the form of a dietary supplement, a dietetic support or of an actual medicine, comprising as characterizing active ingredients: (a) a carnitine selected from the group consisting of acetyl L-carnitine and propionyl L-carnitine or a pharmacologically acceptable salt thereof or mixtures thereof; and (b) an extract of *Ginkgo biloba* or one or more of the ginkgolides isolated from *Ginkgo biloba* or mixtures thereof.

18 Claims, No Drawings

COMPOSITION FOR THE PREVENTION AND/OR TREATMENT OF CIRCULATORY DISORDERS, COMPRISING DERIVATIVES OF L-CARNITINE AND EXTRACTS OF *GINKGO BILOBA*

This application is the US national phase of international application PCT/IT00/00391 filed Oct. 2, 2000 which designated the U.S.

The present invention relates to a composition suitable for the prevention and/or treatment of circulatory disorders both at peripheral and cerebral level.

Correspondingly, the composition may take the form and exert the activity of a dietary supplement or of an actual medicine, depending upon the support or preventive action or the strictly therapeutic action which the composition is intended to exert according to the particular individuals for whom it is to be used.

More specifically, the composition according to the present invention comprises as characterising active ingredients:

(a) a carnitine selected from the group consisting of acetyl L-carnitine and propionyl L-carnitine or a pharmacologically acceptable salt thereof or mixtures thereof, and (b) an extract of *Ginkgo biloba* or one or more of the ginkgolides isolated from *Ginkgo biloba* or mixtures thereof.

The biological and pharmacological properties of the carnitines at both the cardiac level and the vascular and cerebral energy level are very well known.

Both L-carnitine and, to different extents, its analogues such as acetyl L-carnitine and propionyl L-carnitine are capable of exerting a beneficial action both in myocardial insufficiency and in coronary disorders, as well as in peripheral vascular disorders.

These beneficial effects of the carnitines are due to the complex mechanism of action of these substances, relating particularly to the possibility of supplying energy to the various cell and tissue metabolic processes through activation of the metabolic systems of β-oxidation of fatty acids and of enhanced utilisation of glucose or through inhibition of lipid peroxidation processes and a reduction of free radicals.

Of particular interest would appear to be the interaction which L-carnitine and, above all, acetyl L-carnitine exert at the cerebral level.

It has been found, in fact, that acetyl L-carnitine after postischaemic reperfusion can restore the metabolism of the phosphorous-bearing derivatives and of glucose and in general, the cerebral function as well as being capable of preventing the more marked post-ischaemic neurological damages.

The same protective activity of acetyl L-carnitine has also been detected after stroke as well as in relation to the products of peroxidation.

These experimental findings underlie the beneficial clinical effects obtained with acetyl L-carnitine in the various phenomena related to cerebral ageing.

*Ginkgo biloba* extracts also present a pharmacological and clinical activity characterised by a permanent beneficial action at the circulatory level and particularly at the cerebral circulatory level, with the result that significant results have been achieved with its use in the treatment and prevention of both peripheral and, above all, cerebral vascular insufficiency.

*Ginkgo biloba* is a plant of the family Ginkgoaceae originally native to China and Japan, but now widespread throughout Europe and used for many years now in popular medicine as an anti-inflammatory, anti-asthma and anti-cough agent and, more recently, after isolating its active constituents, in a series of diseases characterised by circulatory insufficiency or by inflammatory or degenerative abnormalities induced by peroxidative phenomena, such as atherosclerosis, thrombosis or respiratory disorders.

The analyses carried out on the active constituents present in the leaves of *Ginkgo biloba*, particularly through gas-chromatography (HPLC) analysis, have revealed a multiplicity of chemically and pharmacologically differentiated substances, consisting most notably in the group of the flavonoids, benzoids, diterpenes and sesquiterpenes and in organic acids.

The flavonoids isolated include amentoflavone, bilobetin, isoginkgetin, sciadopitysin, ginkgetin, catechin and epicatechin, isoquercetin, iso-rhamnetol-3-0-rutinoside, kaempferol-3-0-rutinoside, kaempferol-7-0-glucoside, syringetin-3-0-rutinoside, quercetin-3-0-rutinoside, luteolin, kaempferol, quercetin and myricetin.

The benzoids include gallocatechin and epigallocatechin. The diterpenes include ginkgolide A, ginkgolide B, ginkgolide C, ginkgolide J and ginkgolide M.

The sesquiterpenes include bilobalide, and the organic acids include 6-hydroxykinurenic acid, hydroxybenzoic acid, kinurenic acid, ascorbic acid and 3-methoxy-4-hydroxybenzoic acid.

Extensive reports in the literature have shown that all these compounds, both alone and in combination, are capable of exerting an antioxidant action, by scavenging free radicals, a vascular regulatory action and an anti-anoxic action, as well as modulating cerebral energy metabolism.

Most of the studies, especially the clinical trials, have been conducted not only on the compounds isolated from *Ginkgo biloba* extracts, but also on a standardised *Ginkgo biloba* extract containing 24% of glycoside flavonoids and 6% of terpene lactones.

The antioxidant activity of *Ginkgo biloba* extracts has been confirmed by experiments conducted both in vitro and in vivo. It has been observed in vitro that *Ginkgo biloba* extracts are capable of inhibiting the lipid peroxidation of the erythrocyte membranes induced by hydrogen peroxide as well as the peroxidation of the polyunsaturated fatty acids present in the membranes of the hepatic microsomes induced by ferrous ions. It has been observed in vivo that *Ginko biloba* extracts are capable of exerting a protective effect on spinal lesions induced by ischaemia and related to lipid peroxidation. Also very clearly demonstrated is the inhibitory activity of Ginkgo biloba extracts on platelet activating factor (PAF), which is a factor not only recognised as underlying platelet aggregation but also as being responsible for ischaemic circulatory disorders at both the cardiac and cerebral levels. The anti-ischaemic activity of *Ginkgo biloba* extracts has been confirmed in several clinical trials, and such extracts have also proved effective in preventing intermittent claudication and peripheral arteriopathy in general. Diseases related to erectile vascular disorders and tinnitus have shown improvement with the use of *Ginkgo biloba* extracts.

It is in cases of cerebral insufficiency of both vascular and degenerative origin, however, that the use of *Ginkgo biloba* extracts has yielded the most important results. Clinical experiments have demonstrated that the administration of *Ginkgo biloba* extracts is capable of having beneficial effects on senile dementia and on Alzheimer's disease, as well as upon depression, showing, in these studies, too, their superiority over drugs such as tacrine widely used in these conditions.

It has now been surprisingly found that a composition containing as its characterising active ingredients:
(a) a carnitine selected from the group consisting of acetyl L-carnitine and propionyl L-carnitine or a pharmacologically acceptable salt thereof or mixtures thereof, and
(b) an extract of Ginkgo biloba or one or more of the ginkgolides isolated from Ginkgo biloba or mixtures thereof is particularly useful in the prevention and/or treatment of peripheral or central circulatory insufficiency at the myocardial, cerebral and peripheral vascular level, as well as of coronary disorders, nervous depression, insomnia, fatigue, intermittent claudication, tinnitus or penile erectile disorders, cerebral functional deficits, both vascular and metabolic, and articular or gastric inflammatory reactions.

The term "ginkgolides isolated from Ginkgo biloba" is meant to include ginkgolide A, ginkgolide B, ginkgolide C, ginkgolide J and ginkgolide M mentioned above.

The combination of acetyl L-carnitine or propionyl L-carnitine or a pharmacologically acceptable salt thereof or mixtures thereof with a Ginkgo biloba extract has been shown not only to exert a complementary effect of the two types of components, but also a real synergistic effect, revealing a reciprocal enhancement of their activity which may be extremely useful in achieving a safer and more extensive practical utilisation in both the treatment and prevention of disease forms related to cerebral function where both the carnitines and the Ginkgo biloba extract each perform their own useful function.

Experiments conducted by combining the various components of the present invention, in fact, revealed an unexpected and potent synergistic effect which may be clearly demonstrated above all by using those tests which are most predictive with regard to the practical utilisation of the therapeutic or preventive characteristics envisaged for the composition which is the object of the present invention.

One series of experiments conducted by combining a carnitine mixture with Ginkgo biloba extract, i.e. the formulation which is the object of the present invention, has demonstrated the achievement of a potent, unsuspected synergistic action of the individual components leading to a reciprocal enhancement of their effects such as to present the prospect of a more effective use as a food and dietary supplement or even as a drug in the prevention and/or treatment of many circulatory disorders at both the peripheral and cerebral level, the latter including depression, senile dementia and Alzheimer's disease or deficiencies related to ageing.

It has also been found that, advantageously, component (a) may further comprise a "carnitine" selected from the group consisting of L-carnitine, valeryl L-carnitine, isovaleryl L-carnitine and butyryl L-carnitine or their pharmacologically acceptable salts or mixtures thereof.

In the composition according to the present invention, the weight-to-weight ratio of (a) to (b) may range from 20:1 to 5:1, and preferably from 15:1 to 7:1.

The Ginkgo biloba extract may be a liquid, alcoholic, or hydroalcoholic extract, a tincture, a nebulised extract or a dry powder.

Advantageously, the Ginkgo biloba extract comprises at least 24% of glycoside flavonoids and at least 6% of terpenic lactones.

The composition according to the invention may further comprise vitamins, coenzymes, mineral substances, amino acids and anti-oxidants.

EXPERIMENTAL TESTS

PAF-induced Mortality Tests

Platelet-activating factor (PAF) is an acetylated alkyl phosphoglyceride whose release in the body, under various stimuli, causes circulatory-type reactions related mainly to increased capillary permeability, with consequent extravasation of blood, increased platelet aggregation and thrombosis, reduced coronary flow, release of inflammatory factors, lysosomal enzymes and superoxides.

When administered intravenously (20 μg/kg) to animals, PAF causes the death of the animals treated with it in a short space of time, i.e. approximately one hour, mainly as a result of cardiocirculatory collapse.

A series of tests was conducted using the method described by Young (Young J. N., *Prostaglandins* 30:545, 1985) and by Myers (Myers H., *Br. J. Pharmacol.*, 79:595, 1983) in order to assess whether Ginkgo biloba extracts (whose anti-PAF activity is known) protect animals injected with PAF against death and whether the carnitines (particularly propionyl L-carnitine, whose vascular regulatory activity is known) are capable of increasing the protective effect against PAF.

The tests were conducted on albino mice with a mean weight of 25 g divided into various groups, the first of which served as control group and received intravenous injections of PAF at the dose of 20 μg/kg, while the other groups were administered intraperitoneal injections, one hour before to PAF administration, either of Ginkgo biloba extract, or of the various carnitines alone or in combination, or of Ginkgo biloba plus carnitines. The results are shown in Table 1.

The results of these tests indicate that not only Ginkgo biloba extract but also carnitines are capable of affording at least partial protection against death induced by the intravenous injection of PAF, but that the combination of carnitines plus Ginkgo biloba leads to a reciprocal enhancement of the protective effect.

This synergistic action is marked with acetyl L-carnitine, but above all with propionyl L-carnitine or with the various carnitines in combination plus Ginkgo biloba extract.

TABLE 1

PAF-induced mortality tests

| Treatment | | % mortality 1 h after PAF injection |
|---|---|---|
| — | | 100/100 |
| L-carnitine | 300 mg/kg | 90/100 |
| Acetyl L-carnitine | 300 mg/kg | 80/100 |
| Propionyl L-carnitine | 300 mg/kg | 80/100 |
| L-carnitine | 100 mg/kg + | 70/100 |
| Acetyl L-carnitine | 100 mg/kg + | |
| Propionyl L-carnitine | 100 mg/kg | 70/100 |
| Ginkgo biloba extract | 100 mg/kg | 70/100 |
| Acetyl L-carnitine | 300 mg/kg + | 40/100 |
| Ginkgo biloba extract | 100 mg/kg | |
| Propionyl L-carnitine | 300 mg/kg + | 30/100 |
| Ginkgo biloba extract | 100 mg/kg | |
| Acetyl L-carnitine | 100 mg/kg + | 0/100 |
| Propionyl L-carnitine | 100 mg/kg + | |
| L-carnitine | 100 mg/kg + | |
| Ginkgo biloba extract | 100 mg/kg | |

PAF-induced Inflammatory Reaction Tests

In these experiments, a solution containing PAF was injected into the paws of rats according to the method described by Burstein (Burstein S. H., *J. Pharmacol. Exptl. Ther.*, 251:531, 1989).

As is known, PAF injected into the rat paw causes the release of numerous phlogogenic substances, including prostaglandins, which gives rise in a short time to the onset of marked oedema (Bonnet J., *J. Agent Actions*, 11:559, 1981).

Using the method described by Goldenberg (Goldenberg M. M., *Prostaglandins*, 28:271, 1984) and Silva (Silva P. M. R., *Inflammation*, 10:393, 1986), a solution of PAF at an overall dose of 2 µg was injected into the rear paws of rats, and the ensuing oedematous reaction was evaluated with a plethysmographic method according to the technique described by Ferreira (Ferreira S. H., *J. Pharmacol.*, 127:83, 1979).

The tests were conducted in various groups of rats, one of which was a control group, while the others received intraperitoneal administrations, one hour before to PAF injection, of acetyl L-carnitine (300 mg/kg), or propionyl L-carnitine (300 mg/kg), or of a combination of L-carnitine (75 mg/kg), acetyl L-carnitine (75 mg/kg) and propionyl L-carnitine (75 mg/kg), or of a *Ginkgo biloba* extract (100 mg/kg), or of the Ginkgo biloba extract plus carnitines. The results are shown in Table 2.

The results of this test demonstrate that the *Ginkgo biloba* extract and also propionyl L-carnitine and acetyl L-carnitine are capable of reducing the intensity of the PAF-induced oedema, but that the maximum effect is that obtainable with a combination of *Ginkgo biloba* extract plus propionyl L-carnitine or carnitine complex.

In this case, a potent synergistic effect is detected between the inhibitory action of *Ginkgo biloba* and that of the carnitines.

TABLE 2

Inhibition of PAF-induced inflammatory reaction

| Treatment | | % reduction of oedema |
|---|---|---|
| Acetyl L-carnitine | 300 mg/kg | 15 |
| Propionyl L-carnitine | 300 mg/kg | 35 |
| L-carnitine | 300 mg/kg | 10 |
| Acetyl L-carnitine | 100 mg/kg + | 45 |
| Propionyl L-carnitine | 100 mg/kg + | |
| L-carnitine | 100 mg/kg | |
| Ginkgo biloba extract | 100 mg/kg | 35 |
| Acetyl L-carnitine | 300 mg/kg + | 50 |
| Ginkgo biloba extract | 100 mg/kg | |
| Propionyl L-carnitine | 300 mg/kg + | 80 |
| Ginkgo biloba extract | 100 mg/kg | |
| Acetyl L-carnitine | 100 mg/kg + | 90 |
| Propionyl L-carnitine | 100 mg/kg + | |
| L-carnitine | 100 mg/kg + | |
| Ginkgo biloba extract | 100 mg/kg | |

Coronary Spasm Tests

Enhancement of the activity of *Ginkgo biloba* when combined with carnitines was also found on evaluating the effects of the administration of these substances alone and in combination on pitressin-induced experimental coronary spasm.

As is known, intravenous injection of 1 v/kg of pitressin in the rat causes characteristic electrocardiographic abnormalities which are most noticeable in lead II as affecting the T wave (asphyxial T wave) due to the diminished myocardial oxygenation related to the reduced coronary flow caused by the pitressin-induced vascular spasm.

In these tests, before being injected with pitressin, the rats received oral administrations for three days consecutively of 100 mg/kg of *Ginkgo biloba* extracts, or of 300 mg/kg of carnitines alone or carnitine mixture, or of carnitine or carnitine mixture in combination with *Ginkgo biloba*.

As shown from the results in Table 3, both the *Ginkgo biloba* extract and the carnitines (particularly propionyl L-carnitine and the mixture of L-carnitine plus propionyl L-carnitine plus acetyl L-carntine) are capable of exerting a protective effect on coronary spasm, but the maximum effect is that achieved by the combination of *Ginkgo biloba* extract plus carnitines, which affords almost complete protection of the animals thus treated against the signs of coronary spasm, thus revealing in these tests, too, a marked synergistic effect resulting from the activities of *Ginkgo biloba* and the carnitines.

TABLE 3

Inhibition of coronary spasm with pitressin

| Treatment | Rats protected | Weakly protected | Not protected |
|---|---|---|---|
| L-carnitine | 0 | 1 | 3 |
| Propionyl L-carnitine | 2 | 3 | 4 |
| Acetyl L-carnitine | 1 | 3 | 3 |
| L-carnitine + Propionyl L-carnitine + Acetyl L-carnitine | 2 | 4 | 4 |
| Ginkgo biloba extract | | 3 | 3 |
| Propionyl L-carnitine + Ginkgo biloba extract | | 5 | 1 |
| L-carnitine + Ginkgo biloba extract | | 6 | 1 |
| Propionyl L-carnitine + Acetyl L-carnitine + L-carnitine + Ginkgo biloba extract | 9 | 1 | 0 |

Platelet Aggregation Tests

In these tests, blood samples were taken from healthy volunteers with a platelet content of at least $300,000/mm^3$. The method described by Born (Born J. V. R. *J. Physiol.*, 26:25 1963) was used to induce platelet aggregation.

Platelet aggregation was induced by collagen (2.5 µg/ml) and measured both at the beginning and after 10 minutes' incubation with propionyl L-carnitine, acetyl L-carnitine, *Ginkgo biloba* extract or with these compounds in various combinations.

Platelet aggregation was reduced, though only to a slight extent, after incubation either with propionyl L-carnitine or with acetyl L-carnitine and to a significant extent after incubation with *Ginkco biloba* extract.

Platelet aggregaton, however, is almost totally inhibited on combining *Ginkgo biloba* extract with propionyl L-carnitine plus acetyl L-carnitine. The $ED_{50}$s found for the various components used are, in fact, equal to 30.5±0.41 µg for propionyl L-carnitine, 26.4±0.34 µg for acetyl L-carnitine , and 38.4 µg for *Ginkgo biloba* extract. The combination, at the same doses, of *Ginkgo biloba* and propionyl L-carnitine, acetyl L-carnitine or both carnitines together leads to 100% inhibition of the collagen-induced aggregation, thus demonstrating a marked synergistic effect between the carnitines and *Ginkgo biloba*.

Tests of $H_2O_2$ Toxicity on Pheochromocytoma Cells (PC-12)

Lipid peroxidation induced by $H_2O_2$ may appreciably reduce the survival of PC-12 cells. Antioxidant agents added to the culture are capable of reducing the lipid peroxidation damage and prolonging survival (Nordman R., *Free Rad. Biol. Med.*, 1227, 1996). In these tests, a pheochromocytoma cell (PC-12) culture was used containing $3 \times 10^5$ M cells/ml which was submitted for 30 minutes to 0.1 g mM $H_2O_2$.

After 24 hours of observation, the survival of the cells treated with $H_2O_2$ alone was approximately 38%, whereas the survival rose to 45 and 55% when the cells were incubated with propionyl L-carnitine and acetyl L-carnitine (equal to $10^{-8}$ M), respectively, and to 60% when incubated with *Ginkgo biloba* $10^{-4}$ M extract.

The survival of the cells was 85% when propionyl L-carnitine or acetyl L-carnitine were admixed with *Ginkgo biloba* extract at the first concentration used, but was 100% when *Ginkgo biloba* was admixed with both propionyl L-carnitine and acetyl L-carnitine, thus demonstrating the ability of this combination to exert a synergistic protective effect between acetyl L-carnitine, propionyl L-carnitine and *Ginkgo biloba*.

Tests of Protection Against Experimentally Induced Cerebral Ischaemia

Since a major responsible for causing damage following cerebral ischaemia is known to be the production of superoxides and free radicals (Litton S. A., *Nature*, 364:625, 1993), in these tests cerebral ischaemia was brought about by occluding the middle cerebral artery (MCA) of the rat according to the method described by Scharkey (Scharkey Y., *Nature*, 371:336, 1994) by injecting to the anaesthetized animal endothelin-1 (120 pml), for a duration of 3 minutes with a microcannula placed stereotactically in the pyriform cortex at the level of the middle cerebral artery (MCA).

The ischaemic area thus produced was checked after 3 days with transcardiac perfusion of paraformaldehyde solution (4% in PBS).

After removing the brain and placing it in a fixator containing 10% saccharose, cryostat sections were fixed in methyl violet and examined under the optical microscope.

The administration of propionyl L-carnitine (50 mg/kg), acetyl L-carnitine (50 mg/kg) and of a solution of *Ginkgo biloba* (10 mg/kg), or these compounds in combination, was performed intravenously 5 minutes following injection of endothelin-1.

The volume of the infarcted area was calculated according to the method described by Park (Park C., *Anns. Neurol.*, 20:150, 1989). The results are shown in Table 4.

The results of the tests performed demonstrate that the individual compounds used in this experiment exert a distinctly measurable protective action on the formation of ischaemic lesions. However, the maximum effect is that obtainable with the administration of the combination of the various compounds.

In these conditions, in fact, the protection afforded is almost total, thus demonstrating the remarkable and unforeseeable synergistic action which develops when the individual compounds are admixed thus forming the composition of the present invention.

TABLE 4

Tests of cerebral ischaemia induced by endothelin-1 [magnitude of ischaemia (volume mm³) due to MCA occlusion (% reduction in volume compared to controls)]

|  | Volume (mm³) |
|---|---|
| Propionyl L-carnitine | 32.6 ± 2.4 |
| Acetyl L-carnitine | 21.6 ± 1.8 |
| Propionyl L-carnitine + acetyl L-carnitine | 39.2 ± 3.4 |
| Ginkgo biloba | 28.7 ± 2.9 |
| Propionyl L-carnitine + Ginkgo biloba | 78.8 ± 6.5 |
| Acetyl L-carnitine + Ginkgo biloba | 66.5 ± 7.4 |

TABLE 4-continued

Tests of cerebral ischaemia induced by endothelin-1 [magnitude of ischaemia (volume mm³) due to MCA occlusion (% reduction in volume compared to controls)]

|  | Volume (mm³) |
|---|---|
| Propionyl L-carnitine + acetyl L-carnitine + Ginkgo biloba | 92.7 ± 8.1 |

Illustrative, non-limiting examples of compositions according to the invention are reported hereinbelow.

1) Propionyl L-carnitine — 300 mg
   Extract of *Ginkgo biloba* — 40 mg
   (24% of glycosidic flavonoids and 6% of terpenic lactones)
2) Acetyl L-carnitine — 300 mg
   Extract of *Ginkgo biloba* — 40 mg
   (24% of glycosidic flavonoids and 6% of terpenic lactones)
3) Propionyl L-carnitine — 200 mg
   Acetyl L-carnitine — 200 mg
   Extract of *Ginkgo biloba* — 40 mg
   (24% of glycosidic flavonoids and 6% of terpenic lactones)
4) Propionyl L-carnitine — 500 mg
   Extract of *Ginkgo biloba* — 80 mg
   (24% of glycosidic flavonoids and 6% of terpenic lactones)
5) Acetyl L-carnitine — 500 mg
   Extract of *Ginkgo biloba* — 80 mg
   (24% of glycosidic flavonoids and 6% of terpenic lactones)
6) Propionyl L-carnitine — 100 mg
   Acetyl L-carnitine — 100 mg
   L-carnitine — 100 mg
   Valeryl L-carnitine — 100 mg
   Butyryl L-carnitine — 100 mg
   Extract of *Ginkgo biloba* — 40 mg
   (24% of glycosidic flavonoids and 6% of terpenic lactones)
7) Propionyl L-carnitine — 200 mg
   Acetyl L-carnitine — 200 mg
   Extract of *Ginkgo biloba* — 40 mg
   (24% of glycosidic flavonoids and 6% of terpenic lactones)
   Resveratrol — 1 mg
   Extract of *Panax ginseng* — 50 mg
   (24% cf glycosidic flavonoids and 6% of terpenic lactones)
   DHA — 50 mg
   Melatonin — 1 mg
   Vit. E — 5 mg
   Vit. C — 20 mg
   Seleniun methionine — 50 μg
   β-carotene — 10 mg
8) Propionyl L-carnitine — 100 mg
   Acetyl L-carnitine — 100 mg
   L-carnitine — 100 mg
   Extract of *Ginkgo biloba* — 40 mg
   (24% of glycosidic flavonoids and 6% of terpenic lactones)
   Resveratrol — 1 mg
   Extract of *Panax ginseng* — 50 mg
   Coenzyme $Q_{10}$ — 10 mg
   Omega-3 polyunsaturated acids — 100 mg
   Phosphatidylcholine — 100 mg
9) Propionyl L-carnitine — 250 mg
   Acetyl L-carnitine — 250 mg
   Extract of *Ginkgo biloba* — 40 mg
   (24% of glycosidic flavonoids and 6% of terpenic lactones)
   Extract of Hypericum — 100 mg
   (0.3% of hypericin)
   Extract of *Panax ginseng* — 10 mg What is meant by pharmacologically acceptable salt of L-carnitine or alkanoyl L-carnitine is any salt of these active ingredients with an acid that does not give rise to unwanted toxic or side effects. Such salts are well known to pharmacy experts.

Examples of suitable salts, though not exclusively these, are: chloride; bromide; iodide; aspartate, acid aspartate; citrate, acid citrate; tartrate; phosphate, acid phosphate;

fumarate; acid fumarate; glycerophosphate; glucose phosphate; lactate; maleate, acid maleate; orotate; oxalate, acid oxalate; sulphate, acid sulphate, trichloroacetate, trifluoroacetate and methanesulphonate.

A list of FDA-approved pharmacologically acceptable salts is given in Int. J. of Pharm. 33, (1986), 201–217; this publication is incorporated herein by reference.

What is claimed is:

1. A combination composition comprising as characterising active ingredients:
   (a) a mixture of L-carnitine (LC), acetyl L-carnitine (ALC) and propionyl L-carnitine (PLC) or of the pharmacologically acceptable salts thereof; and
   (b) an extract of *Ginkgo biloba* or one or more ginkgolides isolated therefrom or mixtures thereof.

2. The composition of claim 1, wherein the weight ration LC:ALC:PLC is 1:1:1.

3. The composition of claim 1, wherein the ingredient (a) further comprises at least one more carnitine selected from the group consisting of valeryl L-carnitine, isovaleryl L-carnitine and butyryl L-carnitine or their pharmacologically acceptable salts or mixtures thereof.

4. The composition of claim 1, wherein the weight ratio (a):(b) is from 20:1 to 5:1.

5. The composition of claim 1, wherein the weight ratio (a):(b) is from 15:1 to 7:1.

6. The composition of claim 1, wherein the extract of *Ginkgo biloba* is a liquid alcoholic, hydroalcoholic extract, a tincture, a nebulized extract or a dry powder.

7. The composition of claim 1, wherein the extract of *Ginkgo biloba* comprises at least 24% of glycosidic flavonoids and at least 6% of terpenic lactones.

8. The composition of claim 1, wherein the pharmacologically acceptable salt of L-carnitine or of its derivatives is selected from the group consisting of: chloride; bromide; iodide; aspartate, acid aspartate; citrate, acid citrate; tartrate; phosphate, acid phosphate; fumarate, acid fumarate; glycerophosphate; glucose phosphate; lactate; maleate, acid maleate; orotate; oxalate; acid oxalate; sulphate, acid sulphate; trichloroacetate; trifluoroacetate and methane sulphonate.

9. The composition of claim 1, which further comprises vitamins, coenzymes, mineral substances, aminoacids and antioxidants.

10. The composition of claim 1, orally administrable, in the form of a dietary supplement.

11. The composition of claim 1, parenterally, rectally, sublingually or transdermally administrable, in the form of a medicament.

12. The dietary supplement of claim 10, for the treatment of peripheral or central circulatory insufficiency at the myocardial, cerebral, peripheral vascular level or of coronary disorders, nervous depressions, insomnia, fatigue, intermittent claudication, tinnitus, or penile erectile disorders, of both vascular and metabolic cerebral function deficiencies, and of articular or gastric inflammatory reactions.

13. The medicament of claim 11 for the treatment of peripheral or central circulatory insufficiency at the myocardial, cerebral, peripheral vascular level or of coronary disorders, nervous depressions, insomnia, fatigue, intermittent claudication, tinnitus, or penile erectile disorders, of both vascular and metabolic cerebral function deficiencies, and of articular or gastric inflammatory reactions.

14. The dietary supplement of claim 12, in solid, semi-solid or liquid form.

15. The medicament of claim 13, in solid, semi-solid or liquid form.

16. The dietary supplement of claim 14, in the form of tablets, lozenges, pills, capsules, granulates or syrups.

17. The medicament of claim 15, in the form of tablets, lozenges, pills, capsules, granulates, syrups, vials or drops.

18. A therapeutic method for the treatment of peripheral or central circulatory insufficiency at the myocardial, cerebral, peripheral vascular level or of coronary disorders, nervous depressions, insomnia, fatigue, intermittent claudication, tinnitus, or penile erectile disorders, of both vascular and metabolic cerebral function deficiencies, and of articular or gastric inflammatory reactions, which comprises administering to a subject a combination composition comprising the following ingredients:
   (a) a mixture of L-carnitine (LC), acetyl L-carnitine (ALC) and propionyl L-carnitine (PLC) or of the pharmacologically acceptable salts thereof; and
   (b) an extract of *Ginkgo biloba* or one or more ginkgolides isolated therefrom or mixtures thereof.

* * * * *